US008840558B2

(12) United States Patent
Burns

(10) Patent No.: US 8,840,558 B2
(45) Date of Patent: Sep. 23, 2014

(54) METHOD AND APPARATUS FOR MATHEMATICALLY CHARACTERIZING EAR CANAL GEOMETRY

(75) Inventor: Thomas Howard Burns, St. Louis Park, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 731 days.

(21) Appl. No.: 12/478,200

(22) Filed: Jun. 4, 2009

(65) Prior Publication Data
US 2009/0306517 A1 Dec. 10, 2009

Related U.S. Application Data

(60) Provisional application No. 61/059,025, filed on Jun. 5, 2008.

(51) Int. Cl.
*A61B 8/14* (2006.01)
*A61B 5/107* (2006.01)
*A61B 5/00* (2006.01)
*H04R 25/00* (2006.01)

(52) U.S. Cl.
CPC ............ *H04R 25/652* (2013.01); *A61B 5/1076* (2013.01); *A61B 5/6817* (2013.01); *H04R 2225/77* (2013.01)
USPC ......................................................... 600/459

(58) Field of Classification Search
CPC ...... A61B 5/6817; A61B 5/1076; A61B 8/14; H04R 25/652; H04R 2225/77
USPC .......................................... 606/109; 600/459
See application file for complete search history.

(56) References Cited

U.S. PATENT DOCUMENTS

| | | | |
|---|---|---|---|
| 4,190,033 A * | 2/1980 | Foti | 600/555 |
| 5,190,046 A * | 3/1993 | Shturman | 600/463 |
| 5,735,282 A | 4/1998 | Hossack | |

(Continued)

FOREIGN PATENT DOCUMENTS

| | | | |
|---|---|---|---|
| DE | 4135286 C1 | | 1/1993 |
| GB | 2344555 | * | 6/2000 |
| WO | WO-0034739 A2 | | 6/2000 |
| WO | WO-2007004083 A1 | | 1/2007 |

OTHER PUBLICATIONS

European Application Serial No. 10251037.7, Extended European Search Report mailed Oct. 4, 2010, 5 pgs.
European Application Serial No. 10251037.7, Response filed Jun. 7, 2011 to Extended European Search Report mailed Oct. 4, 2010, 7 pgs.
U.S. Appl. No. 12/793,784, Advisory Action mailed May 23, 2013, 3 pgs.
U.S. Appl. No. 12/793,784, Final Office Action mailed Mar. 14, 2013, 24 pgs.

(Continued)

*Primary Examiner* — Long V. Le
*Assistant Examiner* — Bo J Peng
(74) *Attorney, Agent, or Firm* — Schwegman Lundberg & Woessner, P.A.

(57) ABSTRACT

The present subject matter provides apparatus and methods for physically fitting a hearing assistance device, including mathematically characterizing a person's ear canal. The apparatus includes an expandable balloon for positioning in the ear canal, the balloon including a hollow interior channel. A flexible catheter extends through the interior portion of the balloon, and the flexible catheter includes a track. A platform is movably coupled to the track. An ultrasonic transducer and a microelectromechanical systems (MEMS) sensor are coupled to the platform. The ultrasonic transducer scans the ear canal and the MEMS sensor senses motion and position of the transducer. According to various embodiments, a mathematical representation of the ear canal is adapted to be computed using information from the transducer and sensor.

20 Claims, 1 Drawing Sheet

(56) References Cited

U.S. PATENT DOCUMENTS

| | | | |
|---|---|---|---|
| 6,093,150 | A | 7/2000 | Chandler et al. |
| 6,631,197 | B1 | 10/2003 | Taenzer |
| 6,751,494 | B2 | 6/2004 | Collier et al. |
| 7,147,604 | B1 | 12/2006 | Allen et al. |
| 7,175,599 | B2 | 2/2007 | Hynynen et al. |
| 7,878,977 | B2 | 2/2011 | Mo |
| 7,998,073 | B2 | 8/2011 | Roth et al. |
| RE42,803 | E | 10/2011 | Lipson et al. |
| 2001/0020126 | A1* | 9/2001 | Swanson et al. ............ 600/407 |
| 2002/0050518 | A1 | 5/2002 | Roustaei |
| 2003/0051323 | A1 | 3/2003 | Gururaja |
| 2004/0049110 | A1 | 3/2004 | Cai et al. |
| 2004/0107080 | A1 | 6/2004 | Deichmann et al. |
| 2004/0202990 | A1 | 10/2004 | Geiger |
| 2004/0204650 | A1* | 10/2004 | Taylor ........................ 600/459 |
| 2004/0210135 | A1 | 10/2004 | Hynynen et al. |
| 2004/0221853 | A1* | 11/2004 | Miller ..................... 128/207.14 |
| 2005/0018540 | A1 | 1/2005 | Gilbert et al. |
| 2005/0027251 | A1 | 2/2005 | Masters |
| 2005/0065426 | A1* | 3/2005 | Porat et al. .................. 600/407 |
| 2005/0251035 | A1 | 11/2005 | Wong |
| 2007/0016055 | A1 | 1/2007 | Cao et al. |
| 2007/0075997 | A1 | 4/2007 | Rohaly et al. |
| 2008/0199829 | A1 | 8/2008 | Paley et al. |
| 2008/0229832 | A1 | 9/2008 | Huang et al. |
| 2009/0036780 | A1 | 2/2009 | Abraham |
| 2010/0312533 | A1 | 12/2010 | Burns |
| 2012/0016243 | A1 | 1/2012 | Brown et al. |

OTHER PUBLICATIONS

U.S. Appl. No. 12/793,784, Non Final Office Action mailed Aug. 24, 2012, 23 pgs.

U.S. Appl. No. 12/793,784, Response filed May 14, 2013 to Final Office Action mailed Mar. 14, 2013, 8 pgs.

U.S. Appl. No. 12/793,784, Response Filed Dec. 21, 2012 to Non Final Office Action mailed Aug. 24, 2012, 10 pgs.

European Application Serial No. 09162091.4, Extended European Search Report mailed Mar. 5, 2013, 7 pgs.

Dickie, A M, et al., "Ultrasound imaging of the canine tympanic bulla", Research in Veterinary Science, vol. 75, (2003), 121-126.

Hossack, John A, et al., "Improving the characteristics of a transducer using multiple active layers", IEEE Transactions on Ultrasonics, Ferroelectrics and Frequency Control, vol. 40, No. 2, 131-139.

Li, Pai-Chi, et al., "Phase aberration correction on two-dimensional conformal arrays", IEEE Transactions on Ultrasonics, Ferroelectrics, and Frequency Control, vol. 42, No. 1, (1995), 73-82.

Singh, Rahul S, et al., "Simulation, fabrication, and characterization of a novel flexible, conformal ultrasound transducer array", 2007 IEEE Ultrasonics Symposium, (2007), 1824-1827.

Taunaumang, A, "Electromechanical properties of 1-3 piezoelectric ceramic/piezoelectric polymer composites", Journal of Applied Physics, vol. 76, No. 1, (1994), 484-489.

Zhang, Qian, et al., "PVDF Transducers—A Performance Comparison of Single-Layer and Multi-layer Structures", IEEE Transactions on Ultrasonics, Ferroelectrics, and Frequency Control, vol. 44, No. 5,, (1997), 1148-1156.

\* cited by examiner

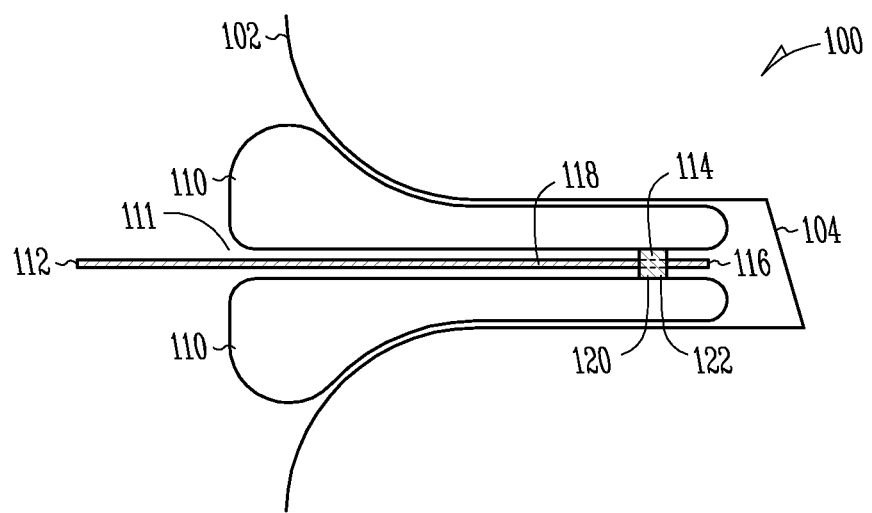

METHOD AND APPARATUS FOR MATHEMATICALLY CHARACTERIZING EAR CANAL GEOMETRY

CLAIM OF PRIORITY

The present application claims the benefit under 35 U.S.C. 119(e) of U.S. Provisional Patent Application Ser. No. 61/059,025, filed Jun. 5, 2008, which is incorporated herein by reference in its entirety.

FIELD OF THE INVENTION

The present application relates to physically fitting hearing assistance devices and in particular to mathematically characterizing ear canal geometry for physically fitting hearing assistance devices.

BACKGROUND

Hearing instrument manufacturers have adopted laser scanning of traditional impressions as the method of obtaining mathematical representations of the ear canal geometry. A dispenser will acquire the impression from the patient and mail the impression directly to the manufacturer. Unfortunately, the impression can become distorted during the mailing process due to uncured material and excessive temperatures in the delivery trucks; the result is an inaccurate impression of the patient's physiology thereby leading to a hearing instrument that does not fit properly. It is common practice for the dispenser to acquire another impression from the patient and return the hearing instrument for rework.

In some instances, it is common for the hearing instrument to pop out of the patient's ear during chewing or other jaw motion. Since the impression is obtained in a "static" condition within the ear canal, geometry changes of the ear canal during chewing can cause the hearing instrument to jostle and pop out. In order to mitigate these occurrences, it may be advantageous to acquire two different impressions: one with the jaw closed and one with the jaw open. The final earmold for the hearing instrument can be extrapolated as an average from the two impressions, thereby reducing the potential for "popout".

Depending on the cure rate of the polymeric material used for ear impressions, the process can typically take from ten to fifteen minutes per pair of impressions, not to mention administrative time in preparing, shipping, and receiving the impressions. It would be advantageous to have a process that acquired the mathematical representation at the dispenser's office in less time and forwarded the data directly to the manufacturer electronically to save time and expense.

SUMMARY

The present subject matter provides apparatus and methods for physically fitting a hearing assistance device, including mathematically characterizing a person's ear canal. The apparatus includes an expandable balloon for positioning in the ear canal, the balloon including a hollow interior channel. A flexible catheter extends through the interior portion of the balloon, and the flexible catheter includes a track. A platform is movably coupled to the track. An ultrasonic transducer and a microelectromechanical systems (MEMS) sensor are coupled to the platform. The ultrasonic transducer scans the ear canal and the MEMS sensor senses motion and position of the transducer. According to various embodiments, a mathematical representation of the ear canal is adapted to be computed using information from the transducer and sensor.

This summary is an overview of some of the teachings of the present application and is not intended to be an exclusive or exhaustive treatment of the present subject matter. Further details about the present subject matter are found in the detailed description. The scope of the present invention is defined by the appended claims and their equivalents.

BRIEF DESCRIPTION OF THE DRAWINGS

FIG. 1 illustrates a cross-section of an ear with a characterizing apparatus positioned for mathematically characterizing the geometry of the ear canal according to one embodiment of the present subject matter.

DETAILED DESCRIPTION

The following detailed description of the present subject matter refers to subject matter in the accompanying drawings which show specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Various embodiments of the present subject matter utilize 1) an ultrasonic transducer system for the purpose of imaging the physiology of the ear canal, 2) a replaceable, fluid-filled medical balloon catheter for the purpose of expanding against the concha and ear canal walls so as to mechanically couple the transducer system to the skin, and 3) a mechanical system to traverse the transducer system within the ear canal in order to image and mathematically compute its shape.

Modem techniques for obtaining a person's ear canal geometry utilize highly-compliant polymeric materials that are injected into a person's ear canal with a syringe. After the material cures, it is pulled from the ear thereby giving a three dimensional impression of the ear canal geometry. Traditionally, the impression is cast in a silicone investment and removed, thereby leaving a representation of the original ear canal. In a procedure that is similar to the traditional casting of a bell, a custom earmold is created by pouring resins into the investment and allowing them to cure into plastic. Although this technique gives a reasonably accurate representation of the ear canal geometry, it does not yield any mathematical information about its shape. A mathematical representation would be valuable for an automated, digital shell making procedure such as stereo lithography, etc.

Recently, laser technology has been used to scan the features of the impression into a mathematical format such as "point cloud" data. These data are used to create a custom shell with automated, digital shell making processes. Unfortunately, the inconvenience of taking a person's ear impression remains the first step in this procedure.

In an effort to preclude the need to "shoot" a person's impression with a syringe of polymeric material, various patents have been filed which use ultrasonic and/or optical devices located on the end of a straight wand. The wand is inserted into the ear canal, and the device scans the geometry. If the device is based on an ultrasonic scanner, the ear canal must be filled with a saline-like fluid thereby making the process inconvenient, messy, and impractical. If the device is based on an optical scanner, complicated mirrors and positioning devices are needed to rotate and control the optical light beam. If the beam is scattered by hair within the ear canal, imaging precision is degraded. In addition, getting useful information beyond the first bend of the ear canal is difficult with a straight wand.

A removable, thin-walled, highly-compliant, elastomeric balloon is pre-formed to fit the physiology of a nominal ear canal and concha. In various embodiments, the physiology of the general population can be characterized with three different pre-formed balloons. The removable balloon is pre-formed with a central, cylindrical, hollow channel, and can be expanded to fit the patient's physiology snugly. The channel contains a conduit for air-pressure relief, a conduit for expanding the balloon with saline or gel, a flexible track and mechanism to position a movable platform, and an ultrasonic transducer probe fixed to the platform. The probe operates in pulse/echo mode and scans the ear canal as the platform is translated and/or rotated down the flexible track. In various embodiments, the transducer system also contains a three-axis microelectromechanical systems (MEMS) gyrator or MEMS accelerator sensor that is used to compute the rate at which the platform is translated and/or rotated. Since the rate at which the platform is translated and/or rotated is known, signal processing can be performed on the acquired ultrasonic and MEMS signal to reconstruct a mathematical representation of the ear canal, much the same way ultrasound is used to image human features inside the human body.

The present subject matter includes a method for scanning and obtaining a mathematical characterization of a person's ear canal geometry, in various embodiments. Various embodiments include a medical balloon that expands with saline within a person's ear canal while relieving internal air pressure to protect the tympanic membrane. A transducer probe transmits and receives ultrasonic acoustical energy within the expanded medical catheter and saline-filled balloon, in an embodiment. Various embodiments include a mechanism that transverses and/or rotates the ultrasonic probe at various locations within the medical catheter and balloon. A method is provided for processing the echoes from the ultrasonic probe and yielding a point cloud mathematical representation of the ear canal geometry, in various embodiments.

FIG. 1 illustrates a cross-section of an ear with a characterizing apparatus positioned for mathematically characterizing the geometry of the ear canal according to one embodiment of the present subject matter. A cross section is depicted of a person's ear canal 100, including pinna 102 and eardrum 104. The apparatus includes an expandable balloon 110 for positioning in the ear canal, the balloon including a hollow interior channel 111. A flexible catheter 112 extends through the interior portion of the balloon, the flexible catheter including a track 118 and conduit 116 for air-pressure relief. A platform 114 is movably coupled to the track. An ultrasonic transducer 120 and a microelectromechanical systems (MEMS) sensor 122 are coupled to the platform. The ultrasonic transducer 120 scans the ear canal and the MEMS sensor 122 senses motion and position of the transducer. According to various embodiments, a mathematical representation of the ear canal is adapted to be computed using information from the transducer and sensor.

This application is intended to cover adaptations or variations of the present subject matter. It is to be understood that the above description is intended to be illustrative, and not restrictive. Thus, the scope of the present subject matter is determined by the appended claims and their legal equivalents.

What is claimed is:

1. A method for mathematically characterizing a person's ear canal, the method comprising:
    positioning a pre-formed expandable balloon in the ear canal, the balloon including a transducer system including a hollow central channel, a flexible catheter extending through the central channel, the flexible catheter including a flexible track, a platform movably coupled to the track, an ultrasonic transducer probe coupled top the platform, and a sensor coupled to the platform;
    expanding the balloon to fit the person's ear canal snugly to mechanically couple the transducer system to the ear canal;
    scanning the ear canal using the ultrasonic transducer probe by moving the platform along the track within the channel and within the balloon, wherein moving the platform includes translating and rotating the platform;
    sensing motion and position of the transducer probe using the sensor; and
    using information from the ultrasonic transducer probe and sensor to compute a mathematical representation of the ear canal.

2. The method of claim 1, further comprising creating a custom hearing assistance device shell for the person using the computed mathematical representation of the person's ear canal.

3. The method of claim 1, wherein the catheter includes a conduit for air-pressure relief to protect the person's tympanic membrane.

4. The method of claim 1, wherein expanding the balloon includes filling the balloon with saline.

5. The method of claim 1, wherein expanding the balloon includes filling the balloon with gel.

6. The method of claim 1, wherein scanning the ear canal using an ultrasonic transducer probe includes operating the probe in pulse/echo mode.

7. The method of claim 1, wherein sensing motion and position of the transducer probe includes using a three-axis gyrator.

8. The method of claim 1, wherein sensing motion and position of the transducer probe includes using a microelectromechanical systems (MEMS) sensor.

9. The method of claim 1, further comprising storing the information from the ultrasonic transducer probe and sensor.

10. The method of claim 1, further comprising transmitting the information from the ultrasonic transducer probe and sensor.

11. A method for mathematically characterizing a person's ear canal, the method comprising:
    inserting a catheter system in the ear canal, the catheter system including a balloon and a flexible track, a platform movably coupled to the track, an ultrasonic transducer probe coupled top the platform, and a sensor coupled to the platform;
    after expanding the balloon to fit the canal and mechanically couple the catheter system to the canal, scanning the ear canal using the ultrasonic transducer probe by translating and rotating the platform along the track within the channel and within the balloon;
    sensing motion and position of the transducer probe using the sensor; and
    using information from the ultrasonic transducer probe and sensor to compute a mathematical representation of the ear canal.

12. The method of claim 11, wherein the sensor includes a microelectromechanical systems (MEMS) sensor.

13. The method of claim 12, comprising characterizing geometry of the ear canal from information from the ultrasonic transducer and the MEMS sensor.

14. The method of claim 11, wherein the ultrasonic transducer includes a probe adapted to transmit and receive acoustical energy within the balloon after expanding the balloon to snugly fit the person's ear canal.

15. The method of claim 11, further comprising storing information from the transducer and sensor in a memory.

16. The method of claim 11, further comprising transmitting information from the transducer and sensor using a communication link.

17. The method of claim 11, wherein scanning the ear canal using an ultrasonic transducer probe includes operating the probe in pulse/echo mode.

18. The method of claim 11, wherein the balloon includes a conduit for air-pressure relief to protect the person's tympanic membrane.

19. The method of claim 11, wherein expanding the balloon includes filling the balloon with saline.

20. The method of claim 11, wherein expanding the balloon includes filling the balloon with gel.

* * * * *